(12) United States Patent
Sato et al.

(10) Patent No.: US 11,779,305 B2
(45) Date of Patent: Oct. 10, 2023

(54) PUNCTURE ADAPTER, ULTRASONIC PROBE, AND ULTRASONIC PROBE UNIT FOR NEEDLE GUIDE ATTACHMENT

(71) Applicant: CANON MEDICAL SYSTEMS CORPORATION, Otawara (JP)

(72) Inventors: Tomohiro Sato, Otawara (JP); Yusuke Kobayashi, Nasushiobara (JP); Hiroyuki Shikata, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/657,150

(22) Filed: Mar. 30, 2022

(65) Prior Publication Data

US 2022/0313212 A1     Oct. 6, 2022

(30) Foreign Application Priority Data

Mar. 31, 2021   (JP) .................................. 2021-061566

(51) Int. Cl.
*A61B 17/34*      (2006.01)
*A61B 8/00*       (2006.01)

(52) U.S. Cl.
CPC ........ *A61B 8/4444* (2013.01); *A61B 17/3403* (2013.01); *A61B 17/3417* (2013.01); *A61B 2017/347* (2013.01); *A61B 2017/3413* (2013.01)

(58) Field of Classification Search
CPC .............. A61B 8/4444; A61B 17/3403; A61B 17/3417; A61B 2017/3413; A61B 2017/347
See application file for complete search history.

(56) References Cited

U.S. PATENT DOCUMENTS

| | | | | |
|---|---|---|---|---|
| 10,507,038 B2* | 12/2019 | Cermak | ............... | A61B 8/0841 |
| 11,497,467 B2* | 11/2022 | Howell | ............... | A61B 8/4422 |
| 2007/0073155 A1* | 3/2007 | Park | ............... | A61B 8/0833 600/461 |
| 2009/0143684 A1* | 6/2009 | Cermak | ............ | A61B 17/3403 600/461 |
| 2010/0081920 A1* | 4/2010 | Whitmore, III | ....... | A61B 5/062 600/424 |
| 2019/0069923 A1* | 3/2019 | Wang | ................. | A61B 17/3403 |

FOREIGN PATENT DOCUMENTS

| | | |
|---|---|---|
| JP | 03-116814 U | 12/1991 |
| JP | 2009-072604 A | 4/2009 |
| JP | 2015-123112 A | 7/2015 |
| WO | WO-2014123161 A1 * 8/2014 ......... A61B 17/3403 |

* cited by examiner

*Primary Examiner* — Angela M Hoffa
*Assistant Examiner* — Amal Aly Farag
(74) *Attorney, Agent, or Firm* — Oblon, McClelland, Maier & Neustadt, L.L.P.

(57) ABSTRACT

A puncture adapter of an embodiment holds a puncture needle and is attached to an ultrasonic probe having an ultrasonic probe group. The puncture adapter has a puncture bracket that can be fixed to the ultrasonic probe and a puncture needle guide that is attached to the puncture bracket. The puncture bracket is not fixed to the ultrasonic probe when the puncture needle guide is not attached. The puncture bracket is fixed to the ultrasonic probe when the puncture needle guide is attached.

15 Claims, 11 Drawing Sheets

PUNCTURE ADAPTER, ULTRASONIC PROBE, AND ULTRASONIC PROBE UNIT FOR NEEDLE GUIDE ATTACHMENT

CROSS-REFERENCE TO RELATED APPLICATION

The present application claims priority based on Japanese Patent Application No. 2021-061566, filed Mar. 31, 2021, the content of which is incorporated herein by reference.

FIELD

Embodiments disclosed in the present description and drawings relate to a puncture adapter, an ultrasonic probe, and an ultrasonic probe unit.

BACKGROUND

In a puncture procedure using an ultrasonic probe, a puncture needle held by a puncture adapter attached to the ultrasonic probe is used. Since such a puncture procedure is performed in a state in which the ultrasonic probe is in direct contact with an organ, for example, the ultrasonic probe is covered with a sheath to prevent stains on the ultrasonic probe. The puncture adapter is attached to the sheathed ultrasonic probe.

Since the puncture needle is subject to a load that presses it to pierce a puncture target position, a sufficient locking force is required for the puncture adapter attached to the ultrasonic probe. In a conventional puncture adapter, for example, an elastic claw portion provided with a protrusion at the tip is moved while shifting with respect to a concave portion, and when the protrusion provided on the claw portion enters the concave portion, the claw portion is locked into a locking portion due to the elasticity of the claw portion. However, since a sufficient locking force is required, there is concern of the sheath being torn due to rubbing between the protrusion of the claw portion and the ultrasonic probe when the claw portion is locked into the concave portion.

SUMMARY OF THE INVENTION

The problem to be solved by embodiments disclosed in the present specification and the drawings is to curb tearing of the sheath when it is attached to the ultrasonic probe. However, the problem to be solved by the embodiments disclosed in the present specification and the drawings is not limited to the above problem. The problem corresponding to each effect of each configuration shown in embodiments which will be described can be positioned as another problem.

A puncture adapter of an embodiment holds a puncture needle and is attached to an ultrasonic probe having an ultrasonic probe group. The puncture adapter has a puncture bracket fixable to the ultrasonic probe and a puncture needle guide attachable to the puncture bracket. The puncture bracket is not fixed to the ultrasonic probe when the puncture needle guide is not attached. The puncture bracket is fixed to the ultrasonic probe when the puncture needle guide is attached.

DETAILED DESCRIPTION

Hereinafter, a puncture adapter, an ultrasonic probe, and an ultrasonic probe unit of an embodiment will be described with reference to the drawings.

Figure 1:
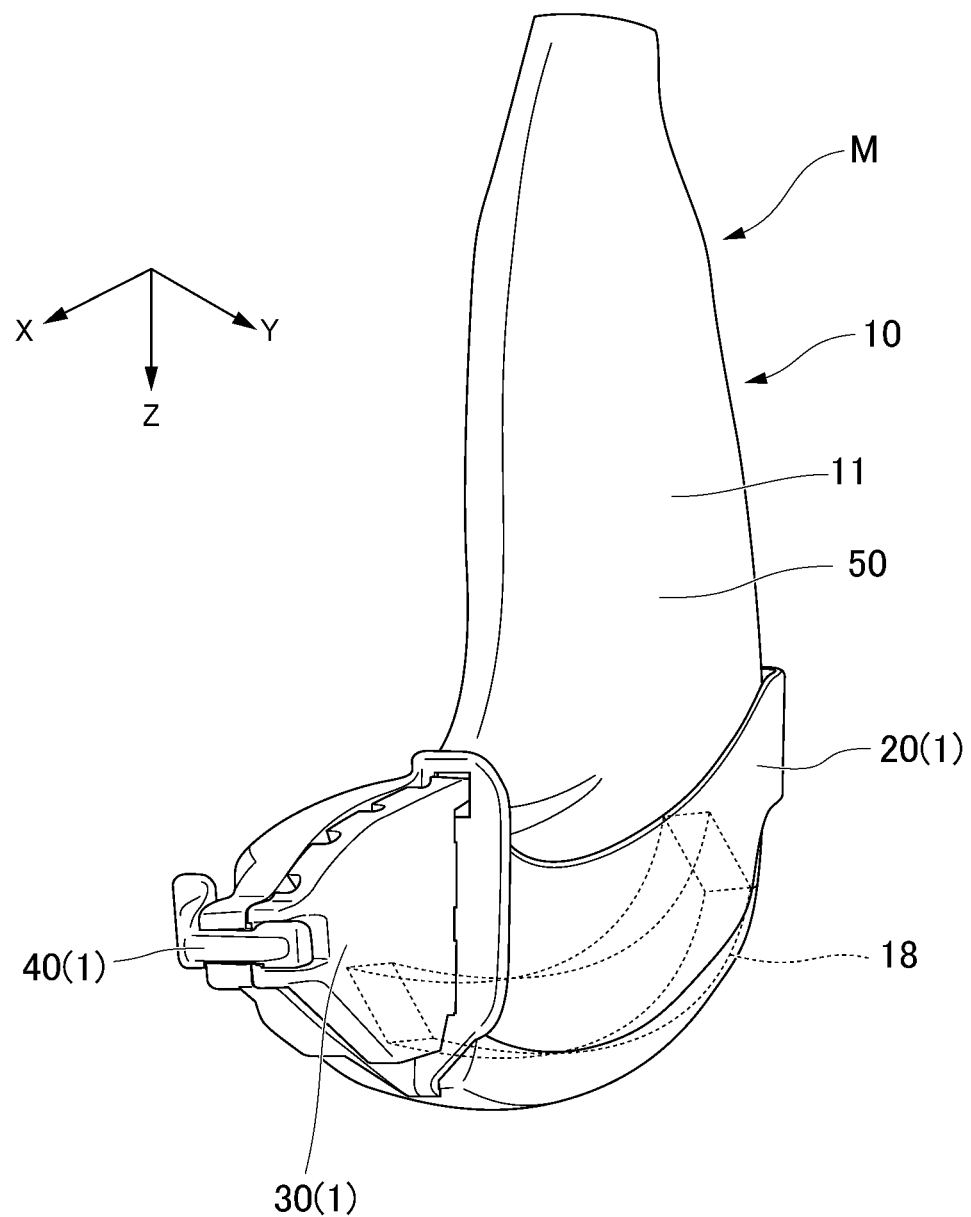
FIG. 1 is a perspective view of an ultrasonic probe unit M.
Figure 2:
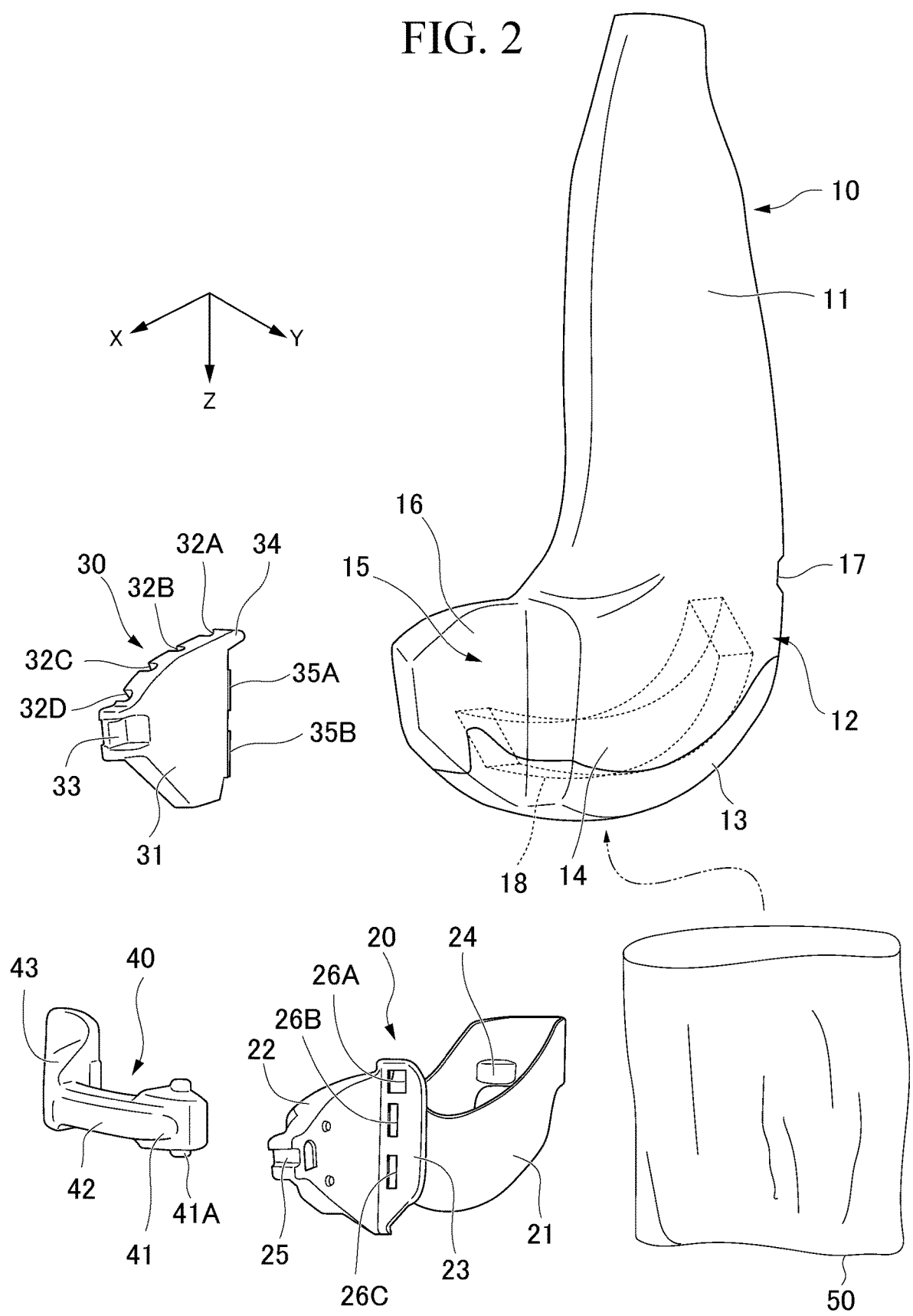
FIG. 2 is an exploded perspective view of the perspective view of the ultrasonic probe unit M.

FIG. 1 is a perspective view of an ultrasonic probe unit M. FIG. 2 is an exploded perspective view of the ultrasonic probe unit M. In the following description, the azimuth direction is the X direction, the elevation direction is the Y direction, and a vibration radiation direction orthogonal to the azimuth direction and the elevation direction is the Z direction. The +X direction is "left," the −X direction is "right," the +Y direction is "forward,", the −Y direction is "rearward," the +Z direction is "down," and the −Z direction is "up" in the following description.

The ultrasonic probe unit M includes a puncture adapter 1 and an ultrasonic probe 10. The puncture adapter 1 can be attached to the ultrasonic probe 10. The ultrasonic probe 10 includes, for example, a handle 11, a head 12, and a transmission/reception surface 13.

The handle 11 is a portion gripped by an operator of the ultrasonic probe 10. A connection cable which is not shown is connected to the opposite side (upper side) of the side (lower side) on which the head 12 is provided in the handle 11. The connection cable is connected to, for example, an ultrasonic diagnostic imaging apparatus which is not shown. Information may be transmitted and received between the ultrasonic probe 10 and the ultrasonic diagnostic imaging apparatus via the connection cable, or by wireless communication or the like without providing the connection cable.

The head 12 has a shape protruding in the +Z direction when viewed from the handle 11. The head 12 includes a head body 14 in which the handle 11 extends in the +Z direction, and a protrusion 15 extending in the +X direction from the head body 14. A notch portion 16 is formed on the side of the protrusion 15.

The notch portion 16 is formed by cutting out the side of the head body 14 in the head 12. The protrusion 15 is a portion remaining after the notch portion 16 of the head body 14 is cut out. The protrusion 15 is provided on the rear side of the head body 14 on the left side. The left side of the head body 14 and the front side of the protrusion 15 correspond to the notch portion 16.

Figure 3:
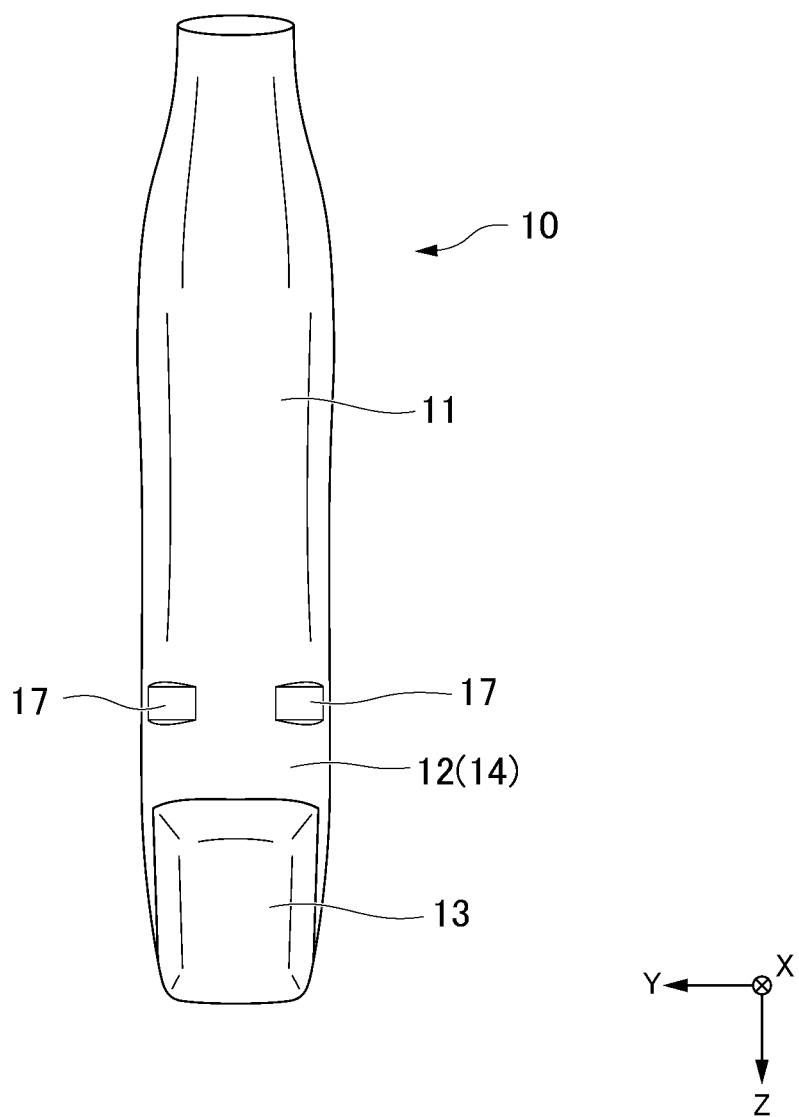
FIG. 3 is a view of an ultrasonic probe 10 from the right.

FIG. 3 is a view of the ultrasonic probe 10 from the right. The end face of the head body 14 in the −X direction is provided with two concave portions 17 that are separated from each other in the Y direction. The concave portions 17 are provided such that the surface of the head body 14 is recessed. The concave portions 17 are an example of a locked portion.

As shown in FIG. 1, an ultrasonic vibrator group 18 that generates ultrasonic waves is provided inside the head 12. The ultrasonic probe 10 transmits the ultrasonic waves generated by the ultrasonic vibrator group 18 from the transmission/reception surface 13 to a subject. The transmission/reception surface 13 receives reflected waves obtained from reflection of the ultrasonic waves by the subject.

The puncture adapter 1 is attached to the ultrasonic probe 10 and holds a puncture needle. The puncture adapter 1 includes, for example, a puncture bracket 20, a puncture needle guide 30, and a fastener 40.

The puncture bracket 20 covers the periphery of a portion avoiding the notch portion 16 from the head 12 of the ultrasonic probe 10. An opening is formed at the bottom of the puncture bracket 20. The transmission/reception surface 13 of the ultrasonic probe 10 is exposed through the opening of the puncture bracket 20.

The ultrasonic probe 10 is covered with a sheath 50. The sheath 50 is a bag-shaped member having flexibility. The puncture adapter 1 is attached to the ultrasonic probe 10 covered with the sheath 50. Accordingly, the sheath 50 is interposed between the ultrasonic probe 10 and the puncture bracket 20.

Figure 4A:
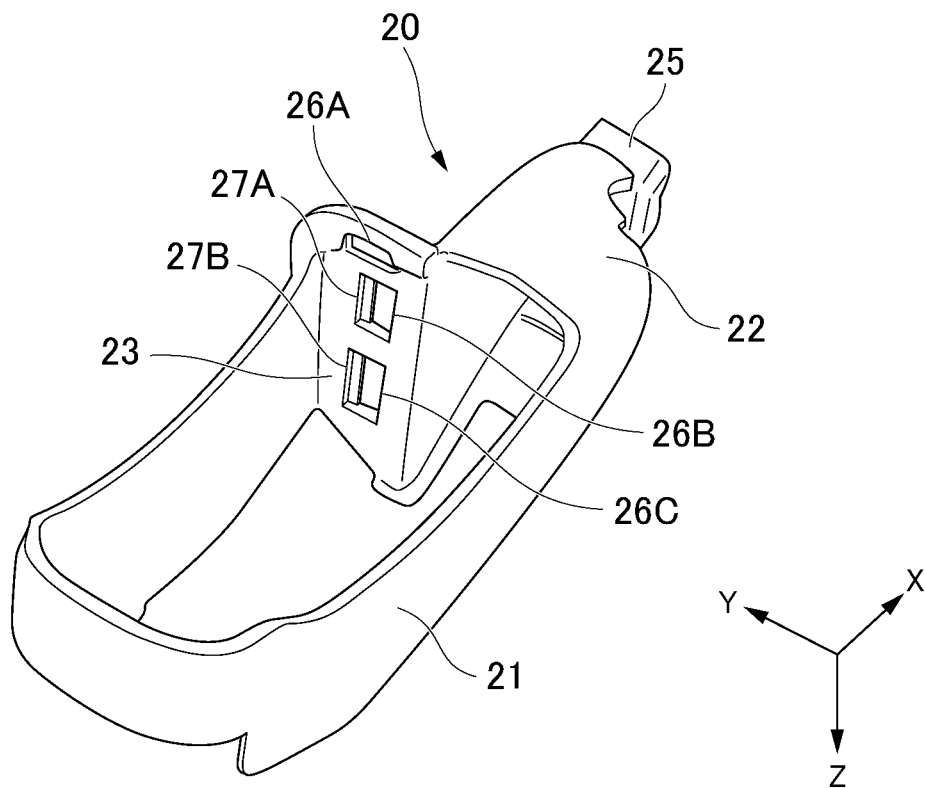
FIG. 4A is a perspective view of a puncture bracket 20.
Figure 4B:
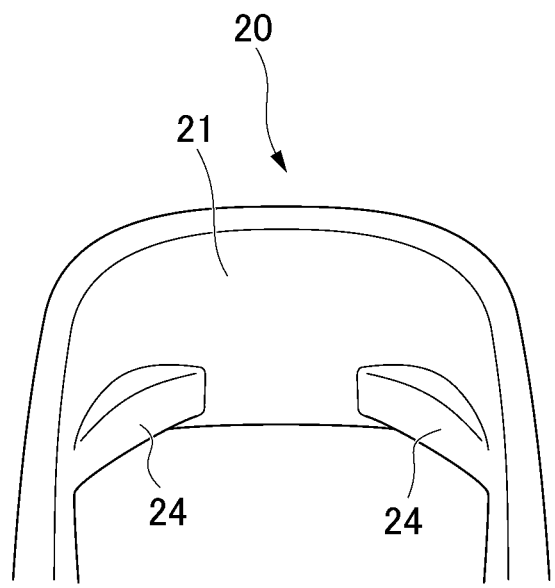
FIG. 4B is an enlarged perspective view of the right end of the puncture bracket 20.

The puncture bracket 20 can be fixed to the ultrasonic probe 10. FIG. 4A is a perspective view of the puncture bracket 20. FIG. 4B is an enlarged perspective view of the right end of the puncture bracket 20. The puncture bracket 20 includes, for example, a first covering portion 21 that covers the side surface of the head body 14, a second covering portion 22 that covers the protrusion 15, and a partition portion 23 disposed at a boundary with the notch portion 16 in the head body 14.

The widths of the first covering portion 21 in the X direction and the Y direction on the inner surface thereof are substantially the same as the widths of the head body 14 in the X direction and the Y direction. Accordingly, the head body 14 is fitted into the first covering portion 21. Since the puncture bracket 20 has elasticity, the sheath 50 covering the ultrasonic probe 10 is sandwiched between the head body 14 and the first covering portion 21.

Two convex portions 24 that are separated in the Y direction are provided on the right inner side of the first covering portion 21. The two convex portions 24 can be fitted into and locked by the two concave portions 17 provided in the head 12 of the ultrasonic probe 10. When the puncture adapter 1 is finally attached to the ultrasonic probe 10, the convex portions 24 are locked by the concave portions 17. The convex portions 24 are an example of a locking portion.

The widths of the second covering portion 22 in the Y direction and the Z direction on the inner surface thereof are substantially the same as the widths of the protrusion 15 in the Y direction and the Z direction. Accordingly, the protrusion 15 is fitted into the second covering portion 22. The sheath 50 covering the ultrasonic probe 10 is sandwiched between the protrusion 15 and the second covering portion 22.

A first receiving portion 25 is provided at the end portion of the second covering portion 22 in the +X direction. A part of the fastener 40 is fitted into the first receiving portion 25 such that the first receiving portion 25 can receive the fastener 40. The partition portion 23 is provided with a first opening 26A, a second opening 26B, and a third opening 26C. The first opening 26A is provided at the end portion of the partition portion 23 in the −Z direction. The second opening 26B is provided at a position deviated from the first opening 26A in the +Z direction, and the third opening 26C is provided at a position deviated from the second opening 26B in the +Z direction.

A first groove 27A and a second groove 27B are provided on the surface of the partition portion 23 on the side of the head body 14 (right side). The first groove 27A is provided on the side of the second opening 26B and the second groove 27B is provided on the side of the third opening 26C. The position where the second groove 27B is provided, viewed from the third opening 26C, is on the same side as the position where the first groove 27A is provided, viewed from the second opening 26B.

Figure 5A:
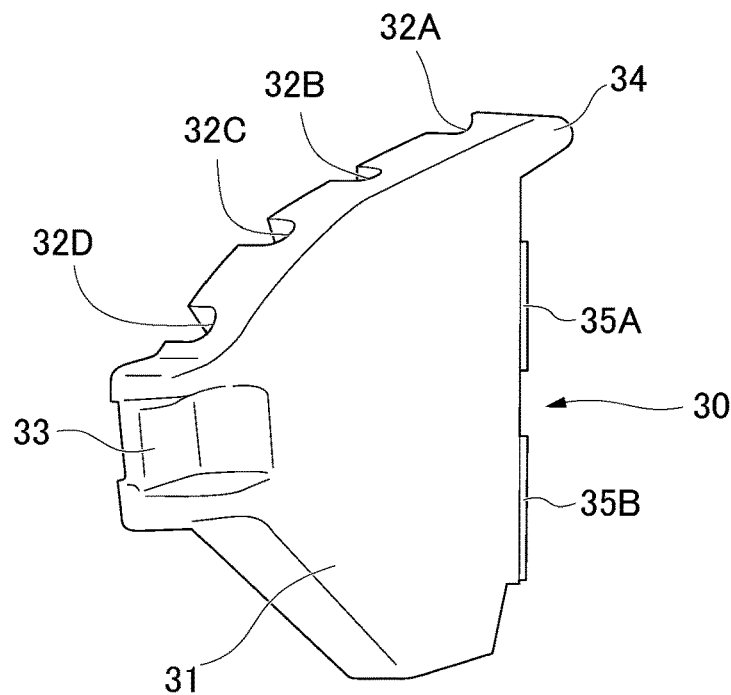
FIG. 5A is a perspective view of a puncture needle guide 30 from the front side.
Figure 5B:
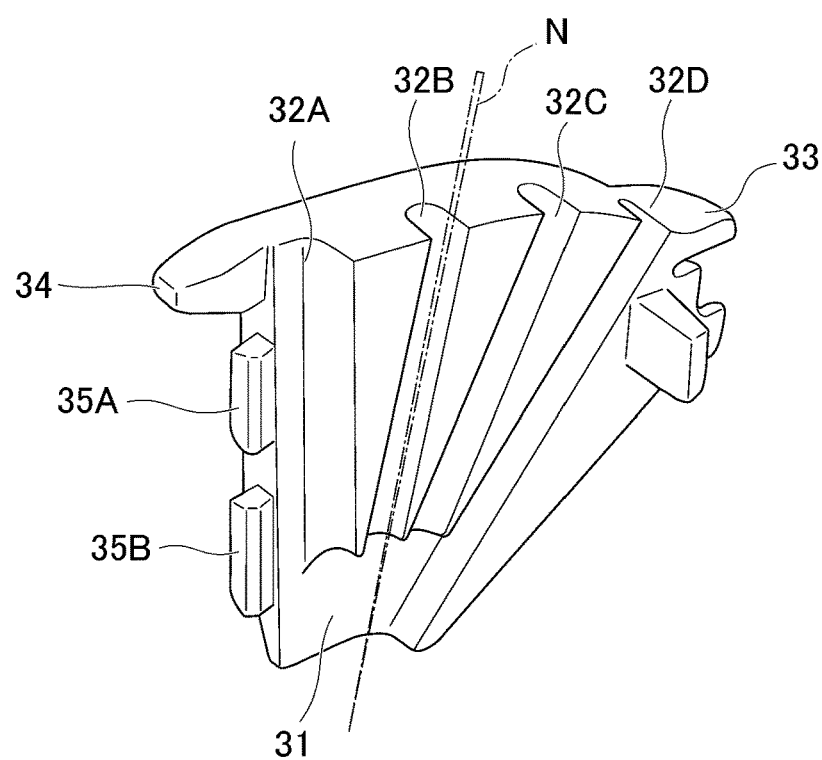
FIG. 5B is a perspective view of the puncture needle guide 30 from behind.
Figure 5C:
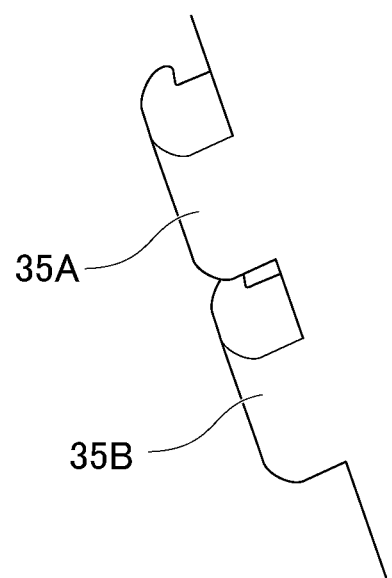
FIG. 5C is an enlarged perspective view of a first claw portion 35A and a second claw portion 35B.

FIG. 5A is a perspective view of the puncture needle guide 30 from the front. FIG. 5B is a perspective view of the puncture needle guide 30 from behind. FIG. 5C is an enlarged perspective view of a first claw portion 35A and a second claw portion 35B. The puncture needle guide 30 includes a guide body 31. A plurality of guide grooves 32, four guide grooves 32 including first to fourth guide grooves 32A to 32D in this embodiment, are provided on the rear side of the guide body 31. A puncture needle N is guided along any one of the first to fourth guide grooves 32A to 32D.

A second receiving portion 33 is provided at the left end portion of the guide body 31. The fastener 40 is attached to the second receiving portion 33. The fastener 40 attached to the second receiving portion 33 is fitted into the first receiving portion 25 such that the relative position of the puncture needle guide 30 with respect to the puncture bracket 20 is fixed.

A stopper 34 protruding to the right is provided above the right end of the guide body 31. The stopper 34 has a size that allows it to be inserted into the first opening 26A formed in the partition portion 23 of the puncture bracket 20. The stopper 34 protrudes to the right from the partition portion 23 of the puncture bracket 20 when the puncture needle guide 30 is attached to the puncture bracket 20 and the puncture adapter 1 is attached to the ultrasonic probe 10. The stopper 34 restrains attachment/detachment of the puncture bracket 20 with the puncture needle guide 30 attached thereto to/from the ultrasonic probe 10. The stopper 34 is an example of a restraining structure.

The first claw portion 35A and the second claw portion 35B which protrude to the right are provided at the right end of the guide body 31. The first claw portion 35A is disposed below the stopper 34 in the guide body 31. The second claw portion 35B is disposed below the first claw portion 35A. The width between the first claw portion 35A and the second claw portion 35B is substantially the same as the width between the second opening 26B and the third opening 26C.

Both the first claw portion 35A and the second claw portion 35B protrude to the right from the end face of the guide body 31. The right ends of the first claw portion 35A and the second claw portion 35B are both bent forward, and the first claw portion 35A and the second claw portion 35B are both formed in a hook shape.

When the puncture adapter 1 has been attached to the ultrasonic probe 10, the first claw portion 35A penetrates the second opening 26B provided in the partition portion 23, and the tip of the first claw portion 35A is hooked to the first groove 27A. At this time, the first claw portion 35A fills a gap between the partition portion 23 of the puncture bracket 20 and the head body 14 of the ultrasonic probe 10. The first claw portion 35A and the second claw portion 35B are examples of a claw portion.

When the puncture adapter 1 has been attached to the ultrasonic probe 10, the second claw portion 35B penetrates the third opening 26C provided in the partition portion 23, and the tip of the second claw portion 35B is hooked to the second groove 27B. At this time, the second claw portion 35B fills the gap between the partition portion 23 of the puncture bracket 20 and the head body 14 of the ultrasonic probe 10 along with the first claw portion 35A.

The fastener 40 includes a tip fitting portion 41, a middle fitting portion 42, and an operation portion 43. The tip fitting portion 41 includes a rotating shaft 41A. The fastener 40 is attached to the puncture needle guide 30 by the tip fitting portion 41 fitting into the second receiving portion 33 provided on the puncture needle guide 30. The fastener 40 is rotatable around the rotating shaft 41A. The fastener 40 may be removable with respect to the puncture needle guide 30.

The thickness of the middle fitting portion 42 is substantially the same as the width of the first receiving portion 25. The middle fitting portion 42 can be fitted into the first receiving portion 25 of the puncture bracket 20. The operation portion 43 can be gripped and operated by an operator. After the tip fitting portion 41 is fitted into the second receiving portion 33, the operator can grip the operation portion and rotate the fastener 40 around the rotating shaft 41A such that the middle fitting portion 42 can be fitted into the first receiving portion 25. After the tip fitting portion 41 is fitted into the second receiving portion 33, the middle fitting portion 42 is fitted into the first receiving portion 25 such that the puncture needle guide 30 is attached to the puncture bracket 20 and the puncture adapter 1 is attached to the ultrasonic probe 10.

Next, a procedure for attaching the puncture adapter 1 to the ultrasonic probe 10 and the operation performed when the puncture adapter 1 is attached to the ultrasonic probe 10 will be described. Before starting the operation of attaching the puncture adapter 1 to the ultrasonic probe 10, the puncture bracket 20 and the puncture needle guide 30 in the puncture adapter 1 are not attached.

When attaching the puncture adapter 1 to the ultrasonic probe 10, the operator first covers the ultrasonic probe 10 with the sheath 50, and completely covers at least the head 12 of the ultrasonic probe 10 with the sheath 50. The sheath 50 covers most or all of the handle 11 along with the head 12, and if a connecting cable is provided, covers all of the ultrasonic probe 10 except for a portion of the handle 11 to which the connecting cable is connected. The sheath 50 may cover the entire ultrasonic probe 10, or if there is a connection cable, may cover the ultrasonic probe 10 including the connection cable.

After covering the ultrasonic probe 10 with the sheath 50, the operator inserts the head 12 of the ultrasonic probe 10 into the upper opening of the first covering portion 21 of the puncture bracket 20 from the upper right. Subsequently, the operator inserts the protrusion 15 of the head 12 into the second covering portion 22 from the right.

Figure 6A:
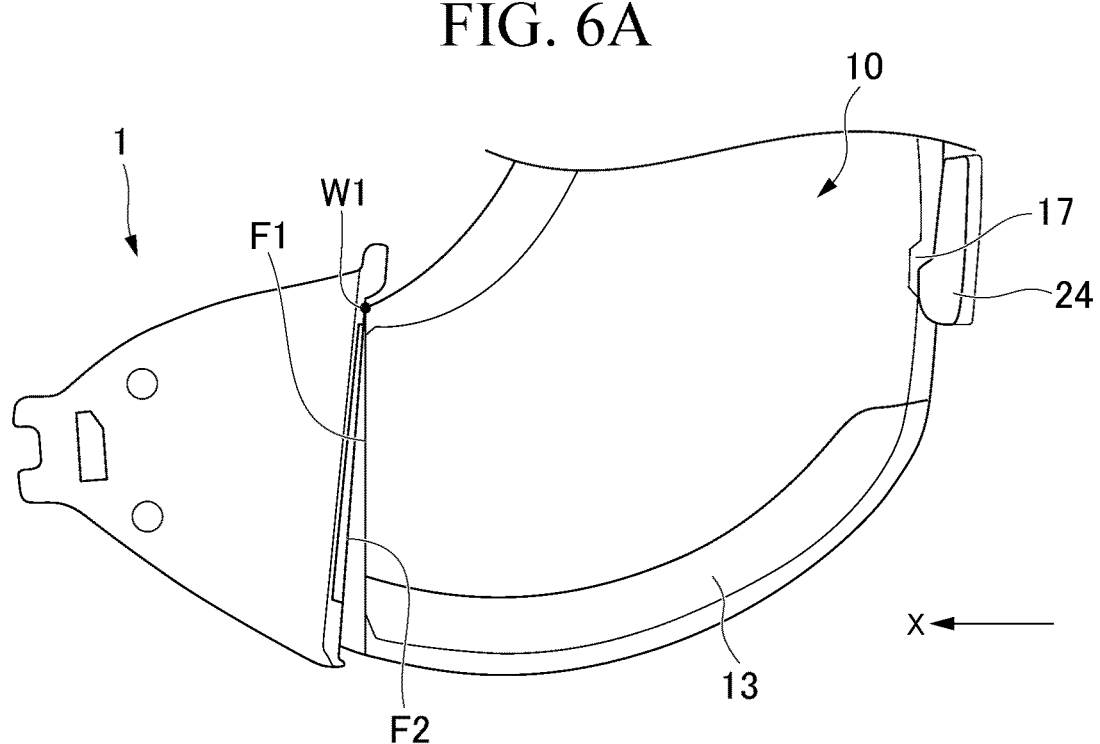
FIG. 6A is a front view of an initial state in which the puncture bracket 20 is attached to the ultrasonic probe 10.
Figure 6B:
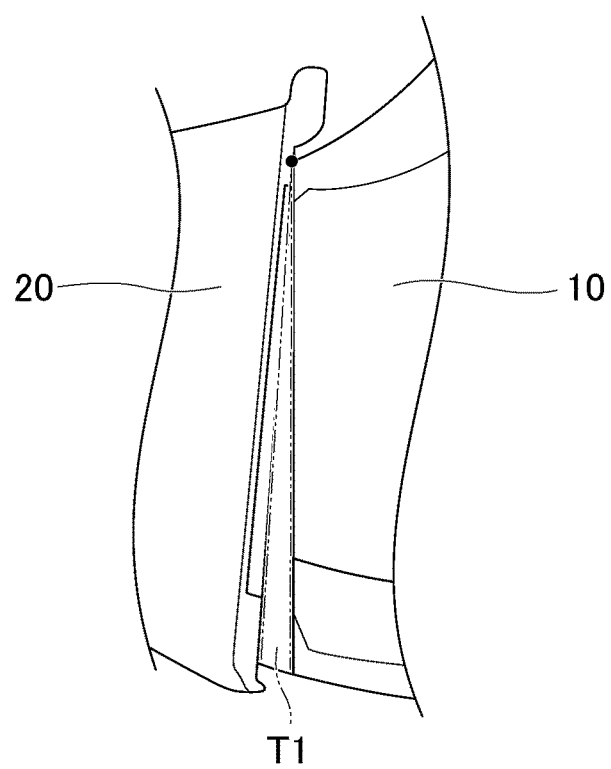
FIG. 6B is an enlarged view of a main part of FIG. 6A.

FIG. 6A is a front view of an initial state in which the puncture bracket 20 is attached to the ultrasonic probe 10, and FIG. 6B is an enlarged view of a main part of FIG. 6A. When the operator inserts the protrusion 15 of the head 12 into the second covering portion 22, a first contact point (contact line) W1 at which the surface of the head 12 on the left side of the puncture bracket 20 and the inner surface of the puncture bracket 20 come into contact with each other is generated, as shown in FIG. 6A. The left side of the puncture bracket 20 is an example of one side of the puncture bracket. According to generation of the first contact point W1, the head 12 cannot be linearly inserted into the puncture bracket 20.

At this time, the concave portion 17 provided in the ultrasonic probe 10 and the convex portion 24 provided in the puncture bracket 20 are separated. As shown in FIG. 6B, a gap in a triangular shape (triangular prism) T1 having the first contact point (contact line) W1 as an apex is formed at a lower position between a surface F1 of the head body 14 of the ultrasonic probe 10 facing the puncture bracket 20 (hereinafter referred to as a first facing surface F1) and a surface F2 of the partition portion 23 of the puncture bracket 20 facing the ultrasonic probe 10 (hereinafter referred to as a second facing surface F2).

In this state, when the lower end of the puncture bracket 20 is moved in the −X direction, the puncture bracket 20 rotates on the first contact point W1 with respect to the ultrasonic probe. The first contact point (contact line) W1 is an example of a rotation axis. This rotation causes the lower part of the puncture bracket 20 to move in the −X direction relative to the ultrasonic probe 10. The convex portion 24 is provided on the opposite side of the first contact point W1 through the ultrasonic probe 10.

Figure 7A:
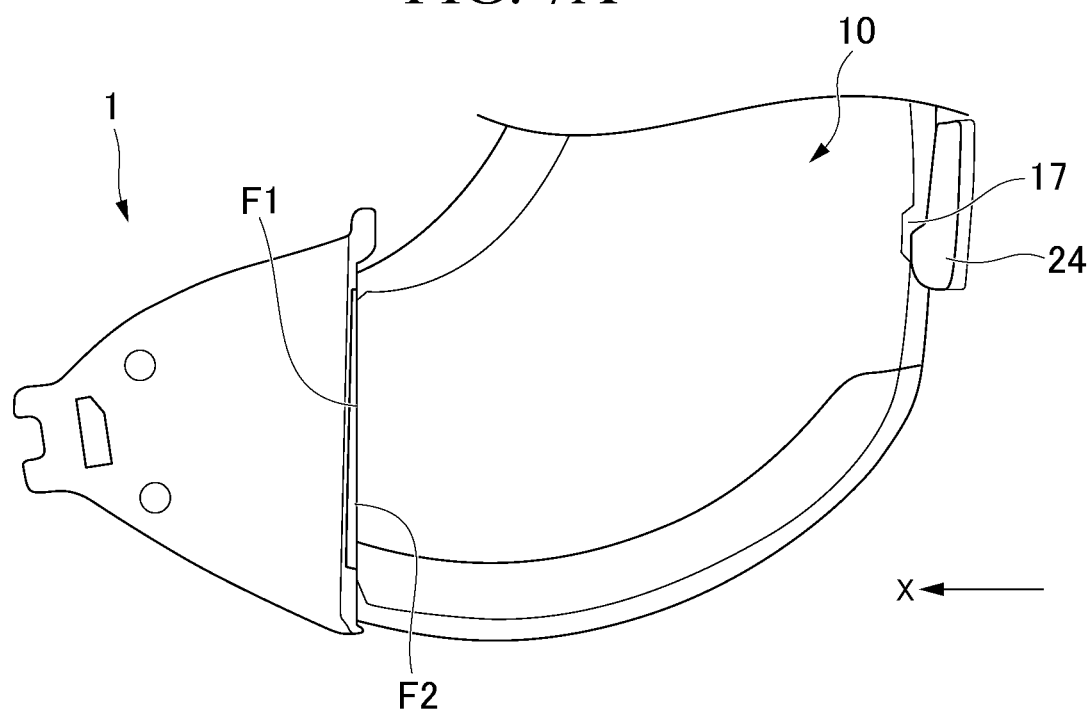
FIG. 7A is a front view of an intermediate state in which the puncture bracket 20 is attached to the ultrasonic probe 10.
Figure 7B:
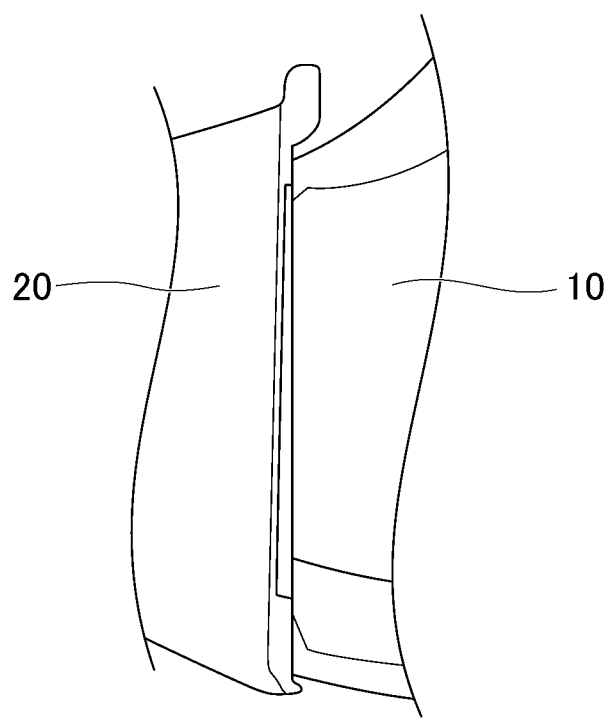
FIG. 7B is an enlarged view of a main part of FIG. 7A.

FIG. 7A is a front view of an intermediate state in which the puncture bracket 20 is attached to the ultrasonic probe 10, and FIG. 7B is an enlarged view of a main part thereof. When the lower part of the puncture bracket 20 moves in the −X direction relative to the ultrasonic probe 10 according to this rotation, the first facing surface F1 and the second facing surface F2 become substantially parallel to each other, as shown in FIG. 7A. When the first facing surface F1 and the second facing surface F2 are substantially parallel to each other, there is almost no gap between the first facing surface F1 and the second facing surface F2, as shown in FIG. 7B. At this time, the concave portion 17 provided in the ultrasonic probe 10 and the convex portion 24 provided in the puncture bracket 20 are close to each other, but are not locked.

Figure 8A:
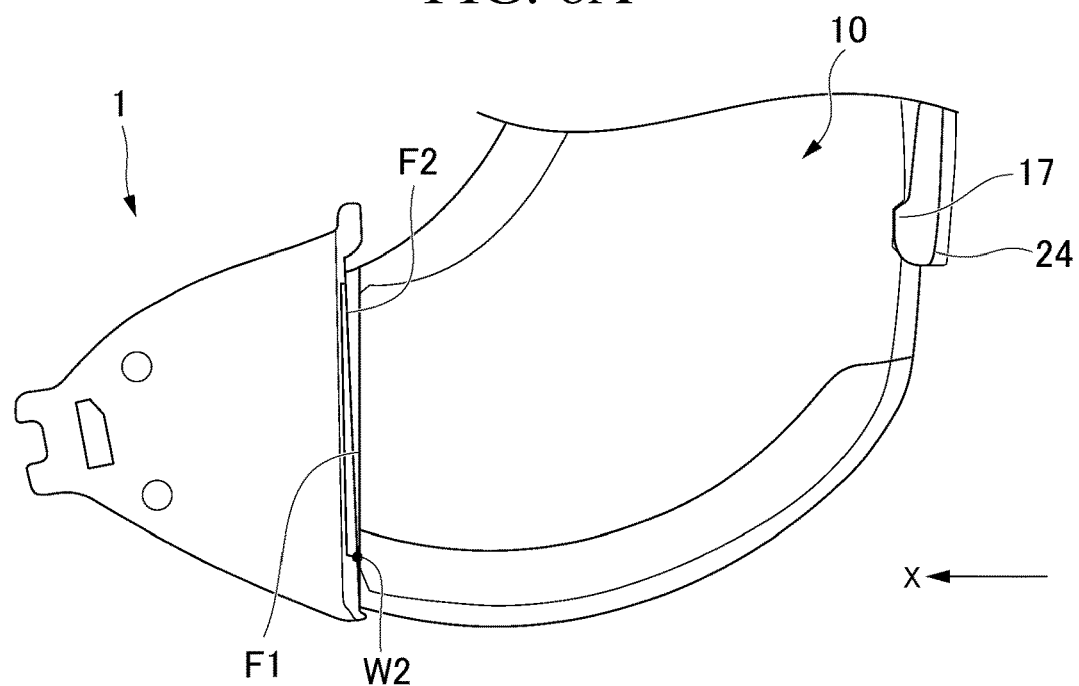
FIG. 8A is a front view of a later state in which the puncture bracket 20 is attached to the ultrasonic probe 10.
Figure 8B:
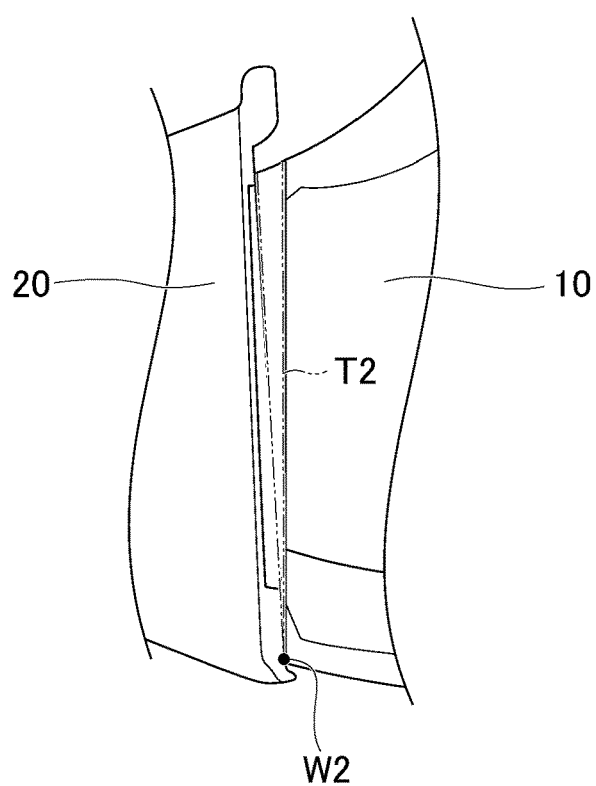
FIG. 8B is an enlarged view of a main part of FIG. 8A.

FIG. 8A is a front view of an intermediate state in which the puncture bracket 20 is attached to the ultrasonic probe 10, and FIG. 8B is an enlarged view of a main part thereof. When the upper end of the puncture bracket 20 is moved in the +X direction in the state in which the concave portion 17 provided in the ultrasonic probe 10 and the convex portion 24 provided in the puncture bracket 20 are close to each other, the puncture bracket 20 rotates on a second contact point (contact line) W2 at which the lower end thereof comes into contact with the ultrasonic probe 10, as shown in FIG. 8A. The upper part of the puncture bracket 20 moves in the +X direction relative to the ultrasonic probe 10 according to this rotation.

When the puncture bracket 20 is continuously rotated, the convex portion 24 enters the concave portion 17 and thus the rotation of the puncture bracket 20 with respect to the ultrasonic probe 10 is restrained. The convex portion 24 enters the concave portion 17 by rotational movement on the second contact point W2. Accordingly, for example, friction due to contact does not occur as in a case where the convex portion 24 is moved linearly along the right side surface of the ultrasonic probe 10. Therefore, when the convex portion 24 is inserted into the concave portion 17 and locked, it is possible to curb damage to the sheath 50 due to friction occurring with the contact between the puncture bracket 20 and the ultrasonic probe 10.

In this state, the convex portion 24 has entered the concave portion 17 and the movement of the puncture bracket 20 with respect to the ultrasonic probe 10 in the Z direction is restrained, but a gap in a triangular shape (triangular prism) T2 having the second contact point (contact point) as an apex has been generated at the upper part between the first facing surface F1 and the second facing surface F2, as shown in FIG. 8B. Accordingly, the puncture bracket 20 is rotatable on the second contact point W2 with respect to the ultrasonic probe 10 in a rotation direction opposite to the rotation direction in which the puncture bracket 20 has rotated so far. Therefore, the concave portion 17 and the convex portion 24 are not locked. The puncture bracket 20 is disposed with a gap with respect to the ultrasonic probe 10 before the convex portion 24 is locked to the concave portion 17. The puncture bracket 20 is not fixed to the ultrasonic probe 10 when the puncture needle guide 30 is not attached.

Subsequently, the first claw portion 35A and the second claw portion 35B of the puncture needle guide 30 are respectively inserted into the second opening 26B and the third opening 26C of the puncture bracket 20. At this time, the stopper 34 of the puncture needle guide 30 is also inserted into the first opening 26A of the puncture bracket 20.

Figure 9A:
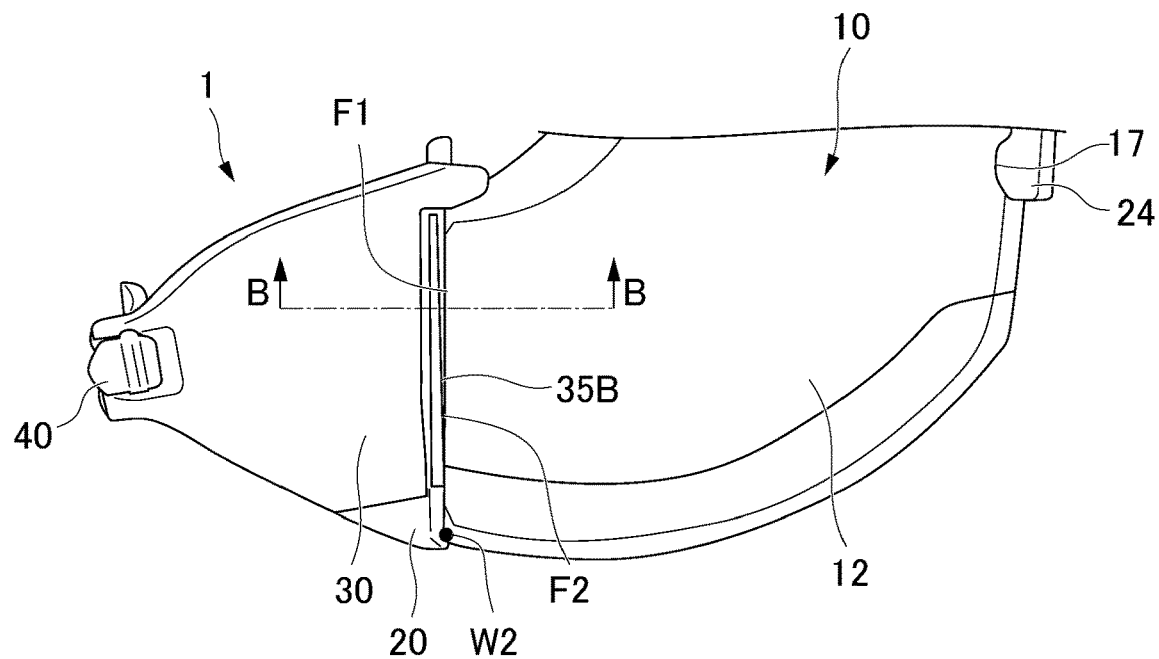
FIG. 9A is a front view of the puncture bracket 20 and the puncture needle guide 30 attached by a fastener 40.
Figure 9B:
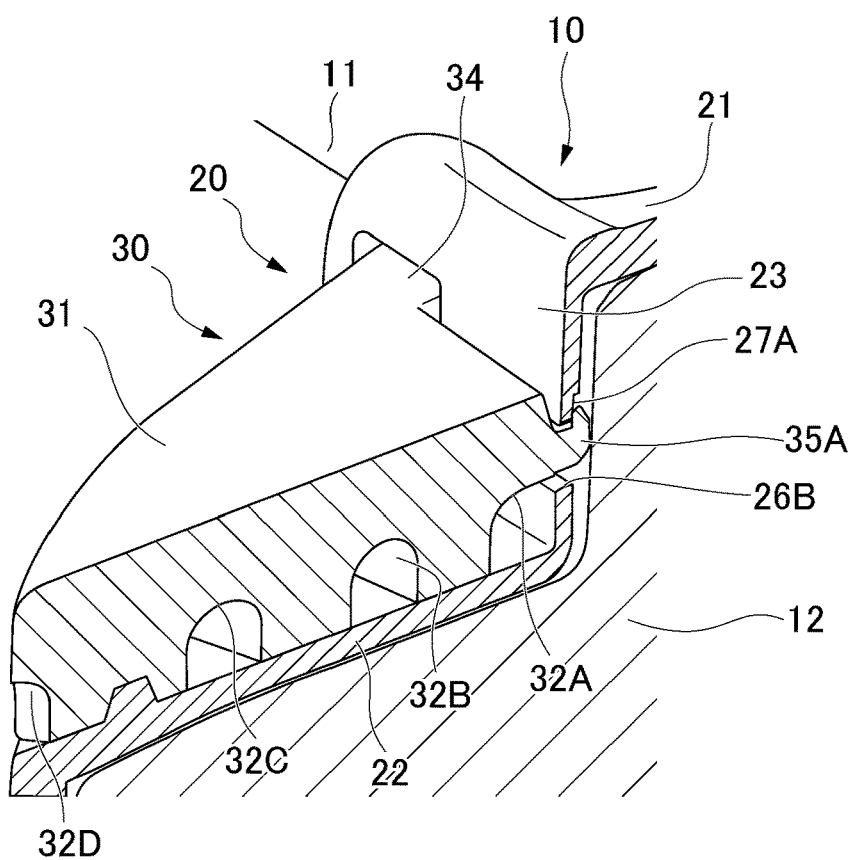
FIG. 9B is a cross-sectional view along line B-B of FIG. 9A.

FIG. 9A is a front view showing a state in which the puncture bracket 20 and the puncture needle guide 30 are attached by the fastener 40. FIG. 9B is a cross-sectional view along line B-B of FIG. 9A. When the puncture needle guide 30 is attached to the puncture bracket 20, the first claw portion 35A and the second claw portion 35B enter between the first facing surface F1 and the second facing surface F2, as shown in FIG. 9A. The first claw portion 35A and the second claw portion 35B that have entered fill the gap between the first facing surface F1 and the second facing surface F2.

When the first claw portion 35A and the second claw portion 35B fill the space between the first facing surface F1 and the second facing surface F2, rotation of the puncture bracket 20 on the second contact point W2 with respect to the ultrasonic probe 10 is restrained, and the convex portion 24 is locked to the concave portion 17. By locking the convex portion 24 to the concave portion 17, the puncture bracket 20 is fixed to the ultrasonic probe 10. The puncture bracket 20 is fixed to the ultrasonic probe 10 according to attachment of the puncture needle guide 30.

As shown in FIG. 9B, the first claw portion 35A and the second claw portion 35B of the puncture needle guide 30 are respectively hooked to the first groove 27A and the second groove 27B (refer to FIG. 4A) of the puncture bracket 20. The puncture needle guide 30 is attached to the puncture bracket 20 by the first claw portion 35A and the second claw portion 35B hooked to the first groove 27A and the second groove 27B.

Thereafter, the operator operates the operation portion 43 such that the fastener 40 attached to the puncture needle guide 30 rotates on the rotating shaft 41A and the middle fitting portion 42 is fitted into the second receiving portion 33 of the puncture needle guide 30. In this way, the puncture needle guide 30 is attached to the puncture bracket 20, and attachment of the puncture adapter 1 to the ultrasonic probe 10 is completed.

At the time of removing the puncture adapter 1 from the ultrasonic probe 10 with which examination is completed, the operator first operates the operation portion 43 of the fastener 40 to rotate the fastener 40 on the rotating shaft 41A counterclockwise (in a direction in which the middle fitting portion 42 becomes far away from the second receiving portion 33) when viewed in the +Z direction and to remove the middle fitting portion 42 from the second receiving portion 33. Subsequently, the operator releases hooking of the first groove 27A and the second groove 27B by the first claw portion 35A and the second claw portion 35B.

After hooking of the first claw portion 35A and the second claw portion 35B is released, the operator pulls the stopper 34, the first claw portion 35A, and the second claw portion 35B out from the first opening 26A, the second opening 26B, and the third opening 26C. When the first claw portion 35A and the second claw portion 35B are pulled out from the second opening 26B and the third opening 26C, the convex portion 24 is released from the locked state with respect to the concave portion 17 and can rotate on the second contact point W2 in the puncture bracket 20.

Subsequently, the operator rotates the puncture bracket 20 on the second contact point W2 clockwise when viewed in the −Y direction. According to rotation of the puncture bracket 20, the convex portion 24 is pulled out in a direction in which it becomes far away from the concave portion 17. In this way, the convex portion 24 is released from the locked state with respect to the concave portion 17. Since the convex portion 24 moves in a direction in which it is separated from the concave portion 17 and is released from the locked state with the concave portion 17, a situation in which the puncture bracket 20 is moved linearly with respect to the ultrasonic probe 10 does not occur when the convex portion 24 moves with respect to the concave portion 17. Accordingly, when the puncture bracket 20 is moved with respect to the ultrasonic probe 10, it is possible to curb damage of the sheath 50 due to friction generated by contact between the ultrasonic probe 10 and the puncture bracket 20.

Thereafter, the puncture bracket 20 is rotated such that the ultrasonic probe 10 and the puncture bracket 20 come into contact with each other at the first contact point W1, and a gap having the first contact point W1 as an apex is formed between the first facing surface F1 and the second facing surface F2. Then, the puncture bracket 20 is moved relative to the ultrasonic probe 10 to be removed from the ultrasonic probe 10. In this way, the entire puncture adapter 1 is removed from the ultrasonic probe 10.

Figure 10A:
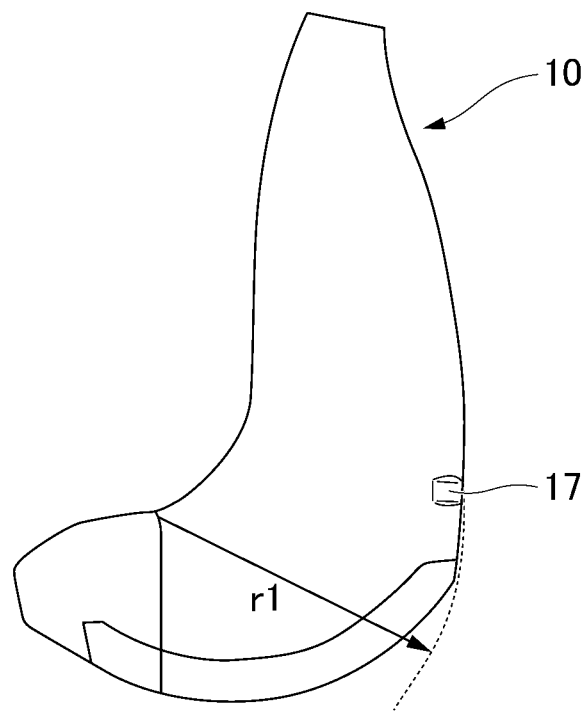
FIG. 10A is a view showing a first radius r1.
Figure 10B:
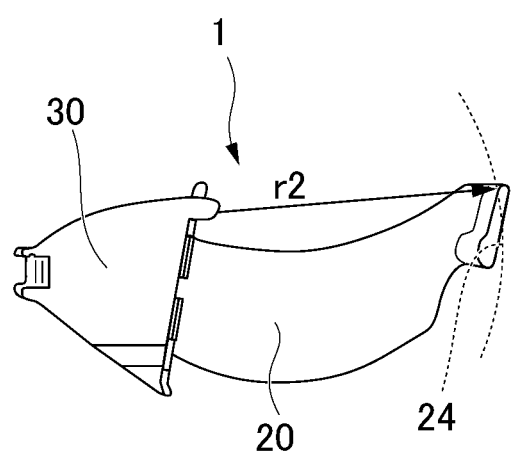
FIG. 10B is a view showing a second radius r2.

In the puncture adapter 1, since the puncture needle guide 30 is provided with the stopper 34, attachment/detachment of the puncture adapter 1 to/from the ultrasonic probe 10 with the puncture needle guide 30 attached to the puncture bracket 20 is restrained. This point will be described below. FIG. 10A is a view showing a first radius r1. FIG. 10B is a diagram showing a second radius r2.

It is assumed that a bracket attachment radius of the ultrasonic probe 10 at the time of attaching the puncture bracket 20 in the ultrasonic probe 10 is a first radius r1, and a probe attachment radius at the time of attaching the puncture bracket 20 in the puncture adapter 1 is a second radius r2. When the puncture needle guide 30 is not provided with the stopper 34, the second radius approximates, for example, the first radius r1.

For example, when the puncture bracket 20 has elasticity and the second radius r2 approximates the first radius r1, a situation in which the puncture adapter 1 is attached to the ultrasonic probe 10 is assumed. In this case, if an external force is applied in the direction in which the convex portion 24 is disengaged from the concave portion 17 and exceeds the locking force (fitting proof stress) between the concave portion 17 and the convex portion 24, it is conceivable that the concave portion 17 and the convex portion 24 are disengaged from each other and thus the puncture bracket 20 is disengaged from the ultrasonic probe 10 to break the sheath 50.

Alternatively, when the puncture bracket 20 has elasticity and the second radius r2 approximates the first radius r1, a situation in which the puncture adapter 1 is to be attached to the ultrasonic probe 10 is assumed. In this case, when the puncture bracket 20 to which the puncture needle guide 30 is attached is to be attached to the ultrasonic probe 10, it is conceivable that a force exceeding the locking force (to-be-fitted proof stress) between the concave portion 17 and the convex portion 24 is applied to the puncture adapter 1, and thus the convex portion 24 is locked to the concave portion 17 to break the sheath 50.

When the stopper 34 is provided on the puncture needle guide 30 and the second radius r2 is sufficiently shorter than the first radius r1, the puncture adaptor 1 attached to the ultrasonic probe 10 cannot rotate due to the relationship between the lengths of the first radius r1 and the second radius r2. Accordingly, the puncture adapter 1 can be prevented from being removed from the ultrasonic probe 10. Furthermore, the puncture adapter 1 before being attached can be prevented from being attached to the ultrasonic probe 10.

According to at least one embodiment described above, the puncture adapter is attached to an ultrasonic probe covered with a sheath and having an ultrasonic vibrator group. The puncture adapter includes a puncture bracket that can be fixed to the ultrasonic probe, and a puncture needle guide attached to the puncture bracket. The puncture bracket is not fixed to the ultrasonic probe when the puncture needle guide is not attached, and is fixed to the ultrasonic probe when the puncture needle guide is attached, and thus can curb damage of the sheath at the time of being attached to the ultrasonic probe.

Although some embodiments have been described, these embodiments are presented as examples and are not intended to limit the scope of the invention. These embodiments can be implemented in various other embodiments, and various omissions, substitutions, and modifications can be made without departing from the gist of the invention. These embodiments and modifications thereof are included in the scope of the invention described in the claims and the equivalent scope thereof, as are included in the scope and gist of the invention.

What is claimed is:

1. A puncture adapter for holding a puncture needle, the puncture adapter being attachable to an ultrasonic probe having an ultrasonic vibrator group and covered with a sheath, the puncture adapter comprising:
    a puncture bracket fixable to the ultrasonic probe covered with the sheath; and
    a puncture needle guide attachable to the puncture bracket,
    wherein the puncture bracket is not fixed to the ultrasonic probe and is disposed with a gap with respect to the ultrasonic probe when the puncture needle guide is not attached, and the puncture bracket is fixed to the ultrasonic probe when the puncture needle guide is attached, and
    the sheath is interposed between the ultrasonic probe and the puncture bracket;
    wherein the puncture bracket is fixed to the ultrasonic probe by locking a locking portion provided on the puncture bracket to a locked portion formed in the ultrasonic probe,
    the puncture bracket is disposed with the gap with respect to the ultrasonic probe before the locking portion is locked to the locked portion, and
    a claw portion provided on the puncture needle guide is inserted into the gap and the puncture needle guide is attached to the puncture bracket, whereby the locking portion is locked to the locked portion.

2. The puncture adapter according to claim 1, wherein the locking portion is a convex portion provided on the puncture bracket, and the locked portion is a concave portion provided in the ultrasonic probe.

3. The puncture adapter according to claim 1, wherein the puncture bracket rotates on a rotation axis on one side of the puncture bracket and is attached to the ultrasonic probe, and the locking portion is provided on the opposite side of the rotation axis via the ultrasonic probe.

4. The puncture adapter according to claim 1, wherein the ultrasonic probe includes a notch portion formed by cutting out a side of a head body in a head, and a protrusion left after the notch portion is cut out, and the puncture bracket covers a periphery of a portion avoiding the notch portion from the head of the ultrasonic probe.

5. The puncture adapter according to claim 2, wherein the puncture bracket includes a first covering portion configured to cover a side surface of the head body and a second covering portion configured to cover the protrusion.

6. The puncture adapter according to claim 5, wherein the head body is inserted into the first covering portion, the protrusion is inserted into the second covering portion, one part of the sheath is sandwiched between the head body and the first covering portion, and another part of the sheath is sandwiched between the protrusion and the second covering portion.

7. The puncture adapter according to claim 6, wherein the concave portion and the convex portion come close to each other, when the head body and the puncture bracket are caused to contact each other at a first contact point and the puncture bracket is caused to rotate on the first contact point.

8. The puncture adapter according to claim 7, wherein, when the concave portion and the convex portion are close to each other, the convex portion enters the concave portion, when the puncture bracket is caused to rotate on a second contact point at which the head body and the puncture bracket contact each other.

9. The puncture adapter according to claim 8, wherein the puncture bracket is fixed to the ultrasonic probe by restraining rotation of the puncture bracket on the second contact point with respect to the ultrasonic probe thereby locking the convex portion into the concave portion.

10. The puncture adapter according to claim 1, wherein the puncture needle guide is provided with a restraining structure configured to restrain attachment/detachment of the puncture bracket to which the puncture needle guide is attached to/from the ultrasonic probe.

11. The puncture adapter according to claim 10, wherein the restraining structure restrains the puncture bracket not to rotate with respect to the ultrasonic probe when the puncture needle guide is attached to the puncture bracket.

12. The puncture adapter according to claim 11, wherein the restraining structure includes a stopper protruding from the puncture bracket when the puncture needle guide is attached to the puncture bracket and the puncture bracket is attached to the ultrasonic probe.

13. The puncture adapter according to claim 12, wherein the stopper is formed on the puncture needle guide.

14. An ultrasonic probe to which a puncture adapter for holding a puncture needle is attachable, the ultrasonic probe having an ultrasonic vibrator group and covered with a sheath, the puncture adapter comprising:
    a puncture bracket fixable to the ultrasonic probe covered with the sheath; and
    a puncture needle guide attachable to the puncture bracket,
    wherein the puncture bracket is not fixed to the ultrasonic probe and is disposed with a gap with respect to the ultrasonic probe when the puncture needle guide is not attached, and the puncture bracket is fixed to the ultrasonic probe when the puncture needle guide is attached, and
    the sheath is interposed between the ultrasonic probe and the puncture bracket,
    wherein the puncture bracket is fixed to the ultrasonic probe by locking a locking portion provided on the puncture bracket to a locked portion formed in the ultrasonic probe,
    the puncture bracket is disposed with the gap with respect to the ultrasonic probe before the locking portion is locked to the locked portion, and a claw portion provided on the puncture needle guide is inserted into the gap and the puncture needle guide is attached to the puncture bracket, whereby the locking portion is locked to the locked portion.

15. An ultrasonic probe unit, comprising:
    a puncture adapter for holding a puncture needle;
    an ultrasonic probe having an ultrasonic vibrator group, to which the puncture adapter is attachable;
    the puncture needle held by the puncture adapter; and
    a sheath that covers the ultrasonic probe, wherein the puncture adapter comprises a puncture bracket fixable to the ultrasonic probe covered with the sheath, and a puncture needle guide attachable to the puncture bracket,
    the puncture bracket is not fixed to the ultrasonic probe and is disposed with a gap with respect to the ultrasonic probe when the puncture needle guide is not attached, and the puncture bracket is fixed to the ultrasonic probe when the puncture needle guide is attached, and
    the sheath is interposed between the ultrasonic probe and the puncture bracket,
    wherein the puncture bracket is fixed to the ultrasonic probe by locking a locking portion provided on the puncture bracket to a locked portion formed in the ultrasonic probe,
    the puncture bracket is disposed with the gap with respect to the ultrasonic probe before the locking portion is locked to the locked portion, and
    a claw portion provided on the puncture needle guide is inserted into the gap and the puncture needle guide is attached to the puncture bracket, whereby the locking portion is locked to the locked portion.

* * * * *